US006482898B1

(12) United States Patent
Yoo et al.

(10) Patent No.: US 6,482,898 B1
(45) Date of Patent: Nov. 19, 2002

(54) HALOGENATED WANG RESINS FOR COMBINATORIAL CHEMICAL SYNTHESIS

(75) Inventors: Sung Eun Yoo, Daejeon (KR); Young Dae Gong, Daejeon (KR); Jin Soo Seo, Daejeon (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 09/762,780
(22) PCT Filed: Aug. 19, 1999
(86) PCT No.: PCT/KR99/00468
§ 371 (c)(1),
(2), (4) Date: Apr. 12, 2001
(87) PCT Pub. No.: WO00/10943
PCT Pub. Date: Mar. 2, 2000

(30) Foreign Application Priority Data

Aug. 20, 1998 (KR) ............................................. 98-33798

(51) Int. Cl.$^7$ .................................................. C08F 8/18
(52) U.S. Cl. ................................ 525/331.4; 525/332.2; 525/359.3

(58) Field of Search ........................... 525/331.4, 332.2, 525/359.3

(56) References Cited

U.S. PATENT DOCUMENTS 6,150,548 A * 11/2000 Koot ........................... 435/7.1
6,180,718 B1 * 1/2001 Boehm et al. .............. 436/518

FOREIGN PATENT DOCUMENTS

| WO | WO 97/42230 | 11/1997 |
| WO | WO 98/50438 | 11/1998 |

* cited by examiner

*Primary Examiner*—Bernard Lipman
(74) *Attorney, Agent, or Firm*—Finnegan, Henderson, Farabow, Garrett & Dunner, L.L.P.

(57) ABSTRACT

The present invention relates to novel halogenated Wang resins for combinational chemical synthesis, more specifically to halogenated Wang resins expressed by formula (1) useful for the effective tracing of combinational chemical synthetic process on solid supports using X-ray photoelectron spectroscopy (XPS) element analysis method; in formula (1), P represents polystyrene-divinylbenzene; X and Y represent hydrogen atom or halogen atom, which may be identical or different, their total number being 1–4; and at least one of them is halogen atom.

6 Claims, 3 Drawing Sheets

HALOGENATED WANG RESINS FOR COMBINATORIAL CHEMICAL SYNTHESIS

BACKGROUND OF THE INVENTION

1. Field of the Invention

The present invention relates to novel halogenated Wang resins for combinatorial chemical synthesis, more specifically to halogenated Wang resins expressed by the following formula 1 useful for the effective tracing of combinatorial chemical synthetic process on solid supports using X-ray photoelectron spectroscopy (XPS) element analysis method.

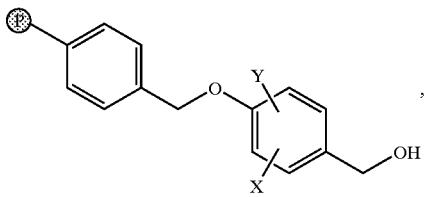

(1)

wherein Ⓟ represents polystyrene-divinylbenzene; X and Y represent hydrogen atom or halogen atom, which may be identical or different, their total number being 1–4; and at least one of them is halogen atom.

2. Description of the Related Arts

Combinatorial chemical synthesis (CCS) is one of the important new methodologies developed by academic and industry researchers in the pharmaceutical, agrochemical, and biotechnological industries to reduce the time and cost. It is a useful tool for rapidly optimizing molecular properties, particularly ones that are difficult to design a prior. Within the past several years, a number of reports have appeared that combinatorial chemistry using solid-phase chemical synthesis provides great potential, because solid-phase chemistry have several big advantages to develop combinatorial techniques such as possible to make a lot of libraries in one pot, simple to purify, simple to continuos multi step reaction, and possible to automation of reaction process.

As explained above, CCS is a new synthetic method which overcomes the uneconomicity and ineffectiveness of the conventional synthetic technologies. However, it was seldom applied to organic synthesis because it was difficult to identify the product of each reaction step and to trace the reaction progress with reaction time.

Solid-NMR spectroscopy, mass spectroscopy and IR spectroscopy are mainly used to trace the reaction progress because CCS is generally performed on the solid support. Solid-NMR spectroscopy has the advantage that the entire structure of the product can be elucidated. However, clear data for the extensive analysis of the product on solid support are hardly obtainable at present. Especially, the structure identification of the compound containing hydrogen and carbon in the same spectral range of the solid support and the quantitative analysis of the reaction progress are highly limited. Mass spectroscopy is effective for small amount of sample and qualitative analysis. However, tracing of reaction progress is highly limited and the qualitative analysis of the various compounds on solid support is very difficult as yet. IR spectroscopy is being used the most widely, because qualitative and approximate quantitative analyses are performed easily. However, if more than one identical functional groups exist in the compound, the quantitative analysis is almost impossible.

The above-mentioned spectroscopic analyses can be partly used for the analysis of compound on solid support. However, the quantitative analysis of reaction progress of the entire chemical reaction on solid support was impossible. So, the determination of the termination point of the chemical reactions on solid support was difficult to compare with the liquid-phase chemical reactions. Accordingly, the reaction was terminated just after long time;

SUMMARY OF THE INVENTION

The inventors of the present invention made repeated researches to find a combinatorial chemical approach in organic synthesis and to introduce a high throughput screening (HTS) method. As a result, we found that X-ray photoelectron spectroscopy (XPS) is effective in the analysis of product and reaction progress on solid support. Developing halogenated Wang resin with new structure, which is useful in XPS analysis and provides excellent chemical stability and reactivity, the present invention was completed.

XPS, which has mainly been applied to polymer synthesis, is not suitable for application to CCS on solid support, because the element amount of the solid support cannot be used as standard amount due to the excessively large (1–2 mmol/resin-1 g) difference of the relative element amount of the solid support and that of the active site.

So, we introduced halogen, a heteroatom, to Wang resin, which is one of the solid supports, in consideration of the fact that most bioactive materials contain heteroatoms. As a result, the relative change of heteroatom during the reaction progress could be traced exactly, and XPS became more effective for elemental analysis.

Accordingly, an object of this invention is to provide a novel halogenated Wang resin useful for CCS and preparing method thereof. Another object of this invention is to provide a quantitative method of analyzing the product produced from the CCS by using halogenated Wang resin and XPS.

DETAILED DESCRIPTION OF THE INVENTION

Figure 1:
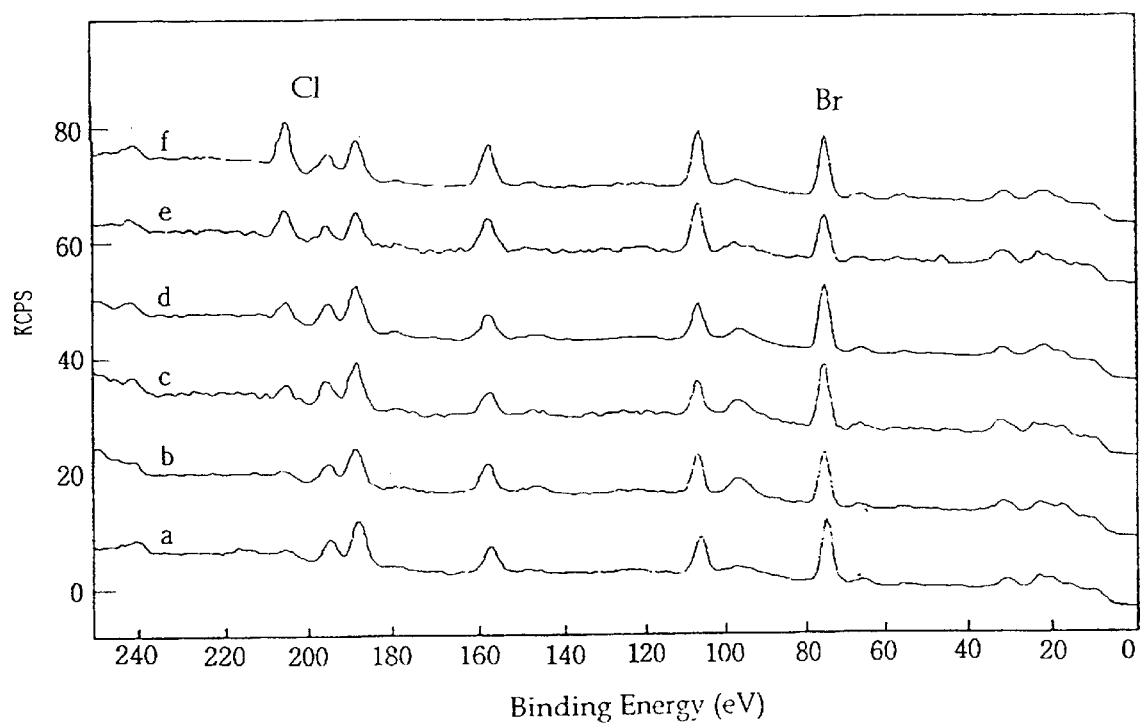
FIG. 1 represents the XPS spectra for the synthesis of 4-chlorobenzoic acid-3-bromo Wang resin.

The present invention is characterized by halogenated Wang resin useful for CCS expressed by the following formula 1.

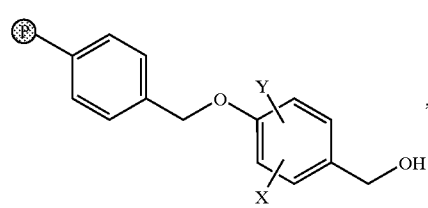

(1)

wherein Ⓟ represents polystyrene-divinylbenzene, and X and Y represent hydrogen atom or halogen atom, which may be identical or different, their total number being 1–4, and at least one of them is halogen atom.

Hereunder is given the detailed explanation of the present invention.

The preparing process of halogenated Wang resin expressed by the above formula 1 comprises (i) a step wherein halogenated 4-hydroxybenzyl alcohol expressed by formula 3 is prepared from 4-hydroxybenzyl alcohol expressed by formula 2, and (ii) a step wherein the compound expressed by formula 3 is reacted with Merrifield resin expressed by formula 4 to prepare halogenated Wang resin expressed by formula 1, as shown in the following scheme 1.

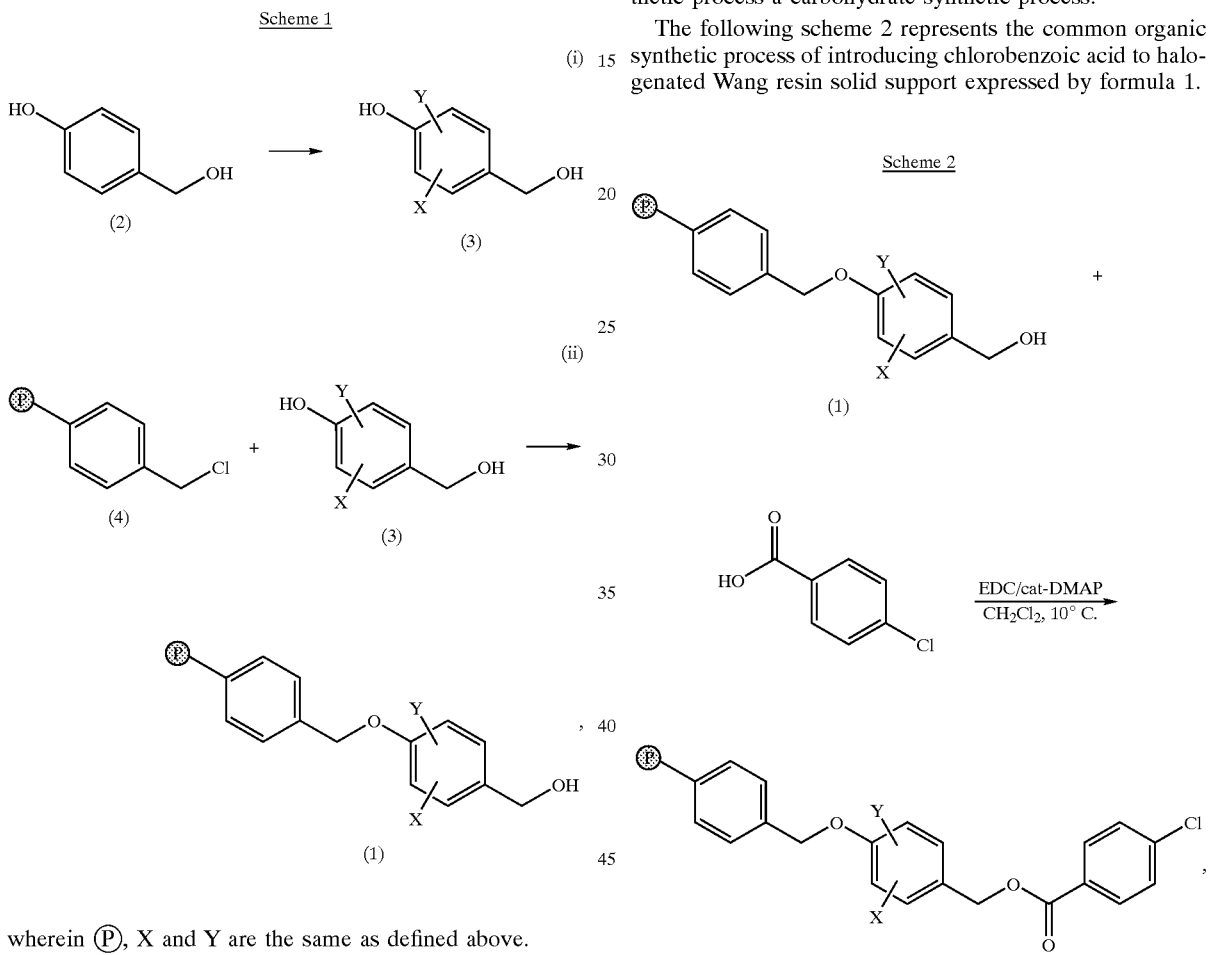

wherein Ⓟ, X and Y are the same as defined above.

Halogenation (i) of scheme 1 is generally performed in the presence of halogenating agent and base. For introduction of bromine atom (Br), it is desired to perform the reaction by using bromine ($Br_2$) as halogenating agent in the presence of $CaCO_3$ base. For introduction of chlorine atom (Cl), it is desired to perform the reaction by using thionyl chloride ($SOCl_2$) as halogenating agent in the presence of ethyl ether. Common organic solvents including dichloromethane are used for the solvent of halogenation, and the reaction is performed normally at room temperature. The amount of halogenating agent used can be controlled depending on the number of halogen functional groups.

Merrifield resin introduction (ii) is performed in the presence of sodium alkoxide or base. Common organic solvents including dichloromethane are used for the solvent, and the reaction is performed normally at room temperature. Sodium alkoxide with 1–4 carbon atoms such as sodium methoxide, sodium ethoxide and sodium isopropoxide, calcium carbonate, triethylamine and diisopropylethylamine are used for the base. After the reaction was performed, no residual Merrifield resin was detected, which was identified by the nonexistence of peak corresponding to chlorine atom (Cl) in identified by the nonexistence of peak corresponding to chlorine atom (Cl) in the XPS spectrum.

The present invention also encompasses the method of exactly tracing the reaction progress through relative XPS elemental analysis of the compound produced from CCS process using halogenated Wang resin expressed by formula 1 as the solid support. Here, CCS process includes all the common organic synthetic processes such as peptide synthetic process a carbohydrate synthetic process.

The following scheme 2 represents the common organic synthetic process of introducing chlorobenzoic acid to halogenated Wang resin solid support expressed by formula 1.

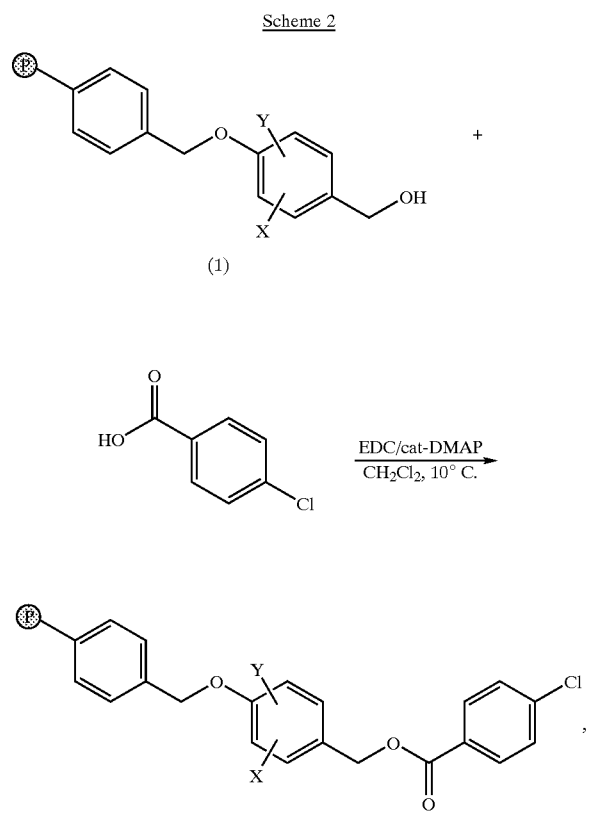

wherein Ⓟ, X and Y are the same as defined above.

Halogenated Wang resin expressed by Formula 1 is reacted with 4-chlorobenzoic acid at 10 C., in the presence of 1-(3-dimethylaminopropyl)-ethylcarbodiimide-hydrochloride (EDC) and catalytic amount of 4-dimethylaminopyridine (DMAP). It is desirable to use 3–5 equivalents of 4-chlorobenzoic acid and EDC to halogenated Wang resin degree of the reaction of scheme 2. The termination point of scheme 2 is the point where the chlorine atom of the functional groups (X or Y) of the solid support becomes 1:1. More detailed reaction condition and the relative XPS elemental analysis results are given in example 2.

The following scheme 3 shows an application of halogenated Wang resin expressed. by formula 1 to peptide chemistry.

Scheme 3

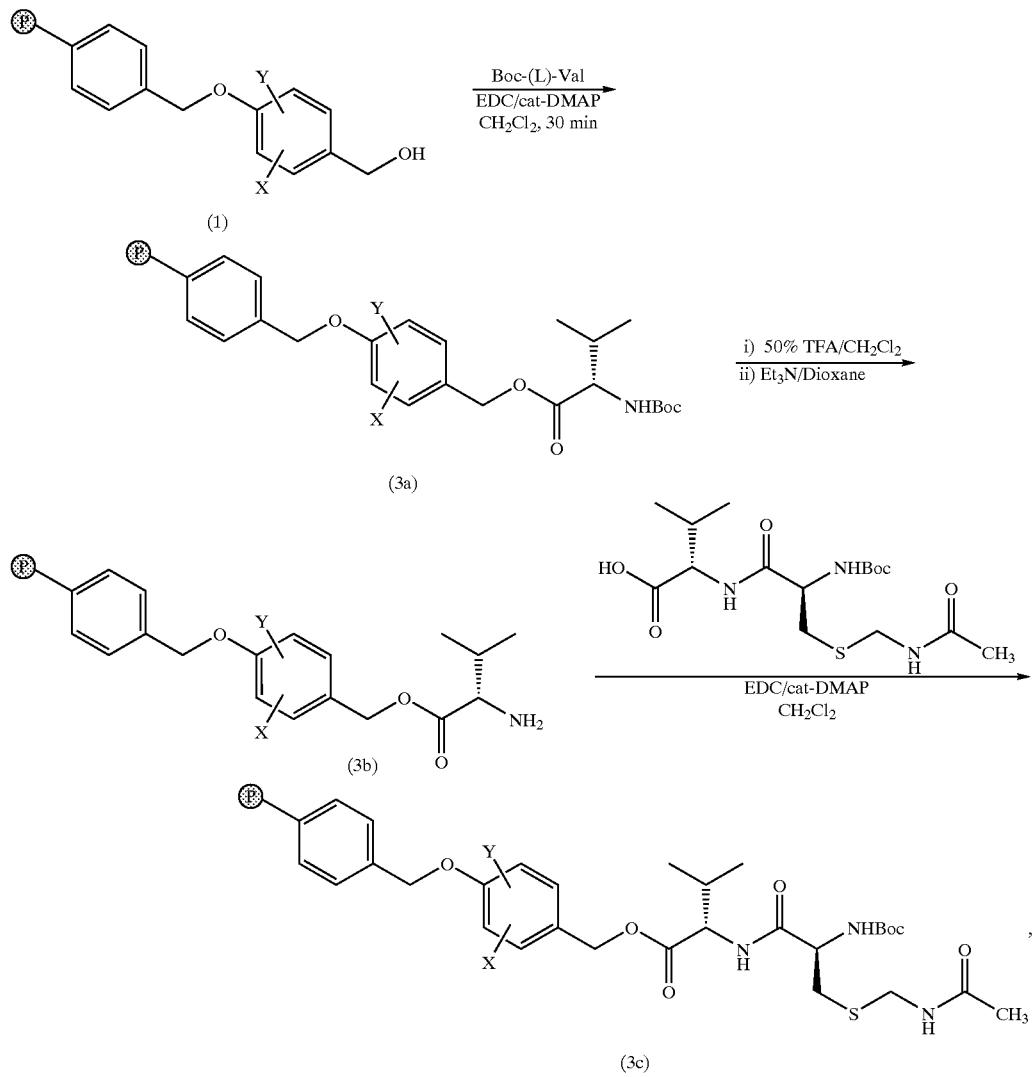

wherein Ⓟ, X and Y are the same as defined above.

Halogenated Wang resin expressed by formula 1 is reacted with valine protected with t-butoxycarbonyl group (Boc-Val) at room temperature for 30 min in the presence of EDC and DMAP to obtain a compound expressed by formula 3a. The compound expressed by formula 3a is reacted in dichloroacetic acid solution of 10% tritiuoacetic acid to remove t-butoxycarbonyl group (Boc), and reacted in 1,4-dioxane solution of 50% triethylamine to obtain amino (Boc), and reacted in 1,4-dioxane solution of 50% triethylamine to obtain amino compound expressed by formula 3b. And then, the amino compound expressed by formula 3b is reacted with cysteine protected with -Boc and acetoamidomethyl group (-Acm) to obtain dipeptide compound expressed by formula 3c.

Various amino acids other than cysteine can be used in peptide synthesis of scheme 3. The degree of peptide formation of scheme 3 was traced using XPS elemental analysis, and it showed that the nitrogen to halogen ratio increases with the increasing number of amino acids. For cysteine, halogen to nitrogen to sulfur ratio increased with increasing number of amino acids. More detailed reaction condition and the results of the relative elemental analysis are given in Example 3.

As explained above, the product formation and reaction progress can be identified quantitatively by XPS elemental analysis if various organic syntheses, such as synthesis of heteroatomic compound and peptide synthesis, are performed using novel halogenated Wang resin, with halogenating linker effective for XPS elemental analysis and having excellent chemical stability and reactivity introduced, as solid support.

The following specific examples are intended to be illustrative of the present invention and should not be construed as limiting the scope of the invention as defined by the appended claims.

EXAMPLE 1

Preparation of 3-bromo Wang resin (3-bromo 4-methoxybenzyl alcohol resin)

(i) Preparation of 3-bromo-4-hydroxybenzyl alcohol (Formula 3) 4-Hydroxybenzyl alcohol (12.4 g, 0.10 mol) and calcium carbonate (20.6 g, 2.06 mol) were dissolved in ethanol (100 ml). After adding ethanol (70 ml) solution containing bromine (7 ml, 0.14 mol) dropwise for 5 hr at −4° C., the same was stirred for 12 hr at 0° C. After the reaction was terminated, 20% sodium thiosulfate solution (150 ml) was added to the reaction mixture. The same was extracted with ethyl acetate (200 ml×3) and the organic layer was washed with water (200 ml×2) and saturated saline water (200 ml). The organic layer was dried over magnesium sulfate anhydride and filtrated. And then, solvent was removed to obtain light brown solid product, which was recrystallized from hexane/ethylacetate (4/1, v/v) solution to obtain 17.25 g (85% yield) of the desired product in the form of light yellow crystal.

$^1$H-NMR (200 MHz, CDCl$_3$): δ10.05 (s, 1H), 7.41 (s, 1H), J=7.10 (d, 1H, J=8.2 Hz), 6.89 (d, 1H, J=8.2 Hz), 5.10 (t, 1H, J=5.6 Hz), 4.37 (d, 2H, J=5.6 Hz)

(ii) Preparation of 3-bromo4-methoxybenzyl alcohol (Formula 1)

3-Bromo-4-hydroxybenzyl alcohol (1.22 g, 6.0 mmol) prepared from i) and sodium methoxide (0.36 g, 6.6 mmol) as base were added to N,N-dimethylformamide (100 ml), and the mixture was stirred for 30 min at room temperature. Chloromethyl resin (Merrifield resin, 1 mmol of chloromethyl site, formula 4; 1.22 g, 2.0 mmol) was added to the reaction solution and stirred for 24 hr at 50° C. The same was filtrated and washed repeatedly with water, methanol and dichloromethane. IR and XPS analyses were performed.

IR: The characteristic peaks of this reaction were hardly distinguishable with IR analysis.

XPS: The point where no more chlorine detected is determined as termination point.

EXAMPLE 2

Introduction of 4-chlorobenzoic acid to 3-bromo Wang resin (i) Introduction of 4-chlorobenzoic acid to 3-bromo Wang resin 3-Bromo Wang resin (1.19 g, 1.2 mmol) prepared from Example 1, 4-chlorobenzoic acid (0.56 g, 3.6 mmol), EDC (0.69 g, 3.6 mmol) and catalytic amount of DMAP (29 mg, 0.24 mmol) were added to dichloromethane (15 ml) at 10° C. 0.1 g of the same was taken with reaction time (5, 10, 20, 30, 50 and 120 min). Each reaction solution was washed with methanol and dichloromethane solvent and dried for XPS elemental analysis.

IR: peak at 1721 cm$^{-1}$ (ii) Tracing of Reaction Progress With Relative XPS Quantitative Elemental Analysis Quantitative XPS elemental analysis with reaction time was performed by calculating the peak height and area of bromine (Br) and chlorine (Cl). The point where area ratio of Br to Cl is ~1:1 is considered as termination point. The results are shown in the following table 1 and FIG. 1.

TABLE 1

| | Reaction time (min) | Area ratio of Cl:Br (%) |
|---|---|---|
| a | 5 | 17.0:83.0 |
| b | 10 | 20.0:80.0 |
| c | 15 | 26.8:73.2 |
| d | 30 | 30.0:70.0 |
| e | 50 | 42.4:57.8 |
| f | 120 | 49.4:50.6 |

FIG. 1 shows that Cl peak migrates to high-energy with reaction time (a→f), while Br peak remains stationary. According to table 1, when the reaction time is 120 min (f), the area ratio of Cl: Br is almost 50:50, and this point can be considered as termination point.

As was shown in example 2, relative XPS quantitative elemental analysis using halogenated Wang resin of the present invention enables the reaction progress to be traced quantitatively. Accordingly, the present invention renders tracing of chemical reaction on solid support and compound analysis possible.

EXAMPLE 3

Application of Relative XPS Elemental Analysis Using 3-bromo Wang resin to Peptide Synthesis (i) Preparation of Boc-Val-3-bromo Wang resin (Formula 3a) and XPS Elemental Analysis 3-Bromo Wang resin (0.3 g, 0.3 mmol) prepared from Example 1, Boc-Val (0.2 g, 0.9 mmol), EDC (0.19 g, 9.9 mmol) and catalytic amount of DMAP (18.0 mg, 0.15 mmol) were added to dichloromethane (10 ml). After stirring for 30 min at room temperature, the reaction solution was filtrated, washed repeatedly with methanol and dichloromethane and dried. The product was analyzed using IR and XPS.

The result of IR analysis showed a broad double-peak corresponding to ester group at 1,717 cm$^{-1}$. However, it was difficult to analyze the amount of Boc-Val introduced Wang resin quantitatively.

Figure 2:
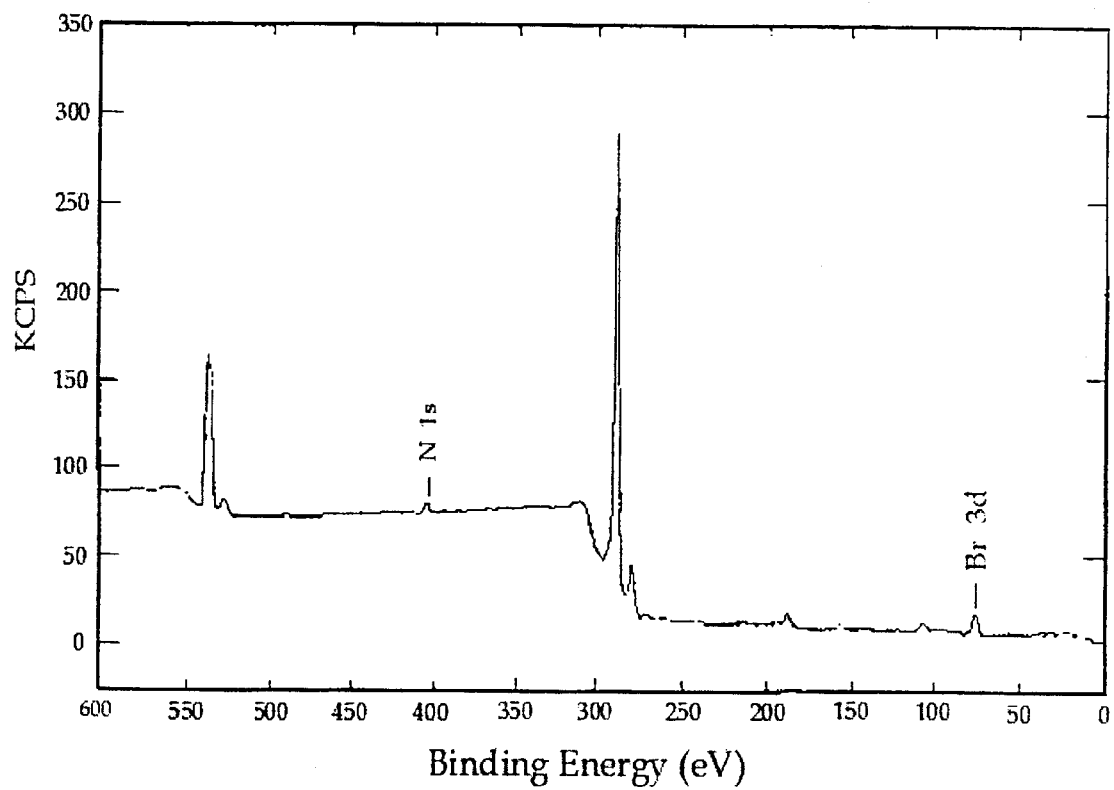
FIG. 2 represents the XPS spectra for the synthesis of Boc-Val-3-bromo Wang resin.

XPS elemental analysis result is shown in the following table 2 and FIG. 2. The area ratio of Br: N at the reaction time of 30 min was 49.2:50.8, which was almost 1:1. Therefore, the termination point of the reaction at room temperature was 30 min.

TABLE 2

| Reaction time (min) | Area ratio of Br:N (%) |
|---|---|
| 30 | 50.2:49.8 |

(ii) Preparation of Boc-Cys-Val-3-bromo Wang resin (Formula 3c) and XPS Elemental Analysis The compound (formula 3a) prepared from (i) of example 3 was reacted in dichloromethane solution of 10% trifluoroacetic acid to remove Boc group, which was the conventional method. The same was neutralized with 1,4-dioxane solution of 50% triethylamine to prepare Val-3-bromo Wang resin (formula 3b).

Val-3-bromo Wang resin (formula 3b; 0.3 g, 0.3 mmol) prepared, Boc-Cys (Acm) (0.27 g, 0.9 mmol), EDC (0.38 g, 0.99 mmol) and t-butyric acid (HOBt; 0.12 g, 0.9 mmol) were added to dichloromethane. After agitating for 30 min at room temperature, the same was filtrated, washed repeatedly with methanol and dichloromethane, and dried. The resulting product was analyzed using IR and XPS.

The result of IR analysis showed a broad double-peak corresponding to ester group at 1,720 cm$^{-1}$. However, it was difficult to analyze the amount of Boc-Cys-Val introduced Wang resin quantitatively.

Figure 3:
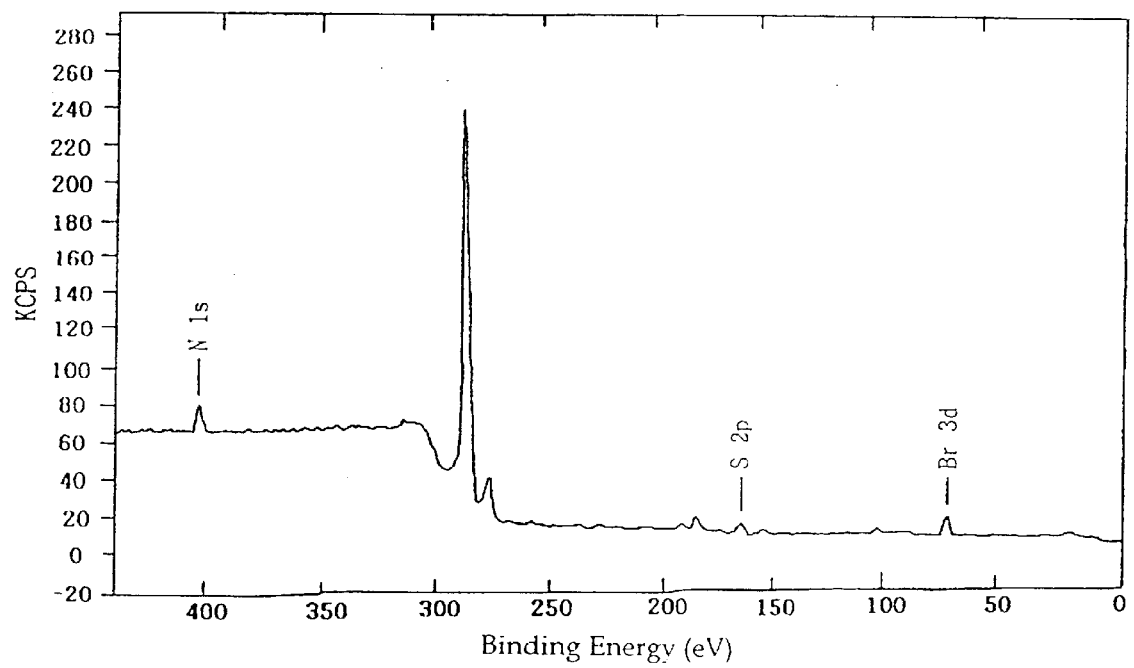
FIG. 3 represents the XPS spectra for the synthesis of Boc-Cys-Val-3-bromo Wang resin.

XPS elemental analysis result is shown in the following table 3 and FIG. 3. The area ratio of Br:S:N at the reaction time of 30 min was 21.1:55.9:22.9, which means that the reaction almost reached the termination point.

TABLE 3

| Reaction time (min) | Area ratio of Br:S:N (%) |
|---|---|
| 30 | 21.1:55.9:22.9 |

As was elucidated in the above Examples, the present invention performs CCS using novel halogenated Wang resin, with halogenating linker containing identical amount of heteroatom to the reactive site introduced, as solid support. The reaction progress can be analyzed quantitatively using XPS elemental analysis.

Accordingly, the present invention facilitates the search of the lead compound with new structure and optimization of its structure and function.

What is claimed is:

1. Halogenated Wang resin expressed by the following formula 1, which is useful for combinatorial chemical synthesis,

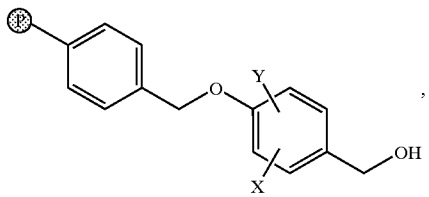

wherein Ⓟ represents polystyrene-divinylbenzene; X and Y represent hydrogen atom or halogen atom, which may be identical or different, their total number being 1–4; and at least one of them is halogen atom.

2. Preparing method of halogenated Wang resin expressed by formula 1, which comprises:

(a) halogenating 4-hydroxybenzyl alcohol expressed by the following Formula 2 to halogenated 4-hydroxybenzyl alcohol expressed by the following formula 3; and (b) reacting the compound expressed by formula 3 with Merrifield resin expressed by the following formula 4 to prepare halogenated Wang resin expressed by formula 1,

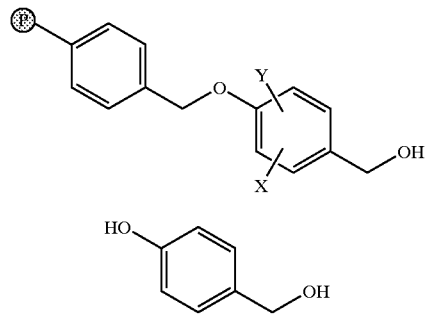

(1)

(2)

-continued

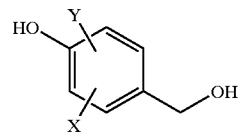

(3)

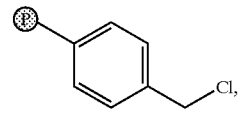

(4)

wherein Ⓟ represents polystyrene-divinylbenzene; X and Y represent hydrogen atom or halogen atom, which may be identical or different, their total number being 1–4; and at least one of them is halogen atom.

3. Preparing method of halogenated Wang resin according to claim 2, wherein the said halogenation is performed using bromine ($Br_2$) or thionyl chloride ($SOCl_2$) as halogenating agent.

4. Preparing method of halogenated Wang resin according to claim 2, wherein the introduction to Merrifield resin is performed in the presence of sodium alkoxide or base.

5. Quantitative analysis using XPS (X-ray photoelectron spectroscopy) of the product of combinatorial chemical synthesis using halogenated Wang resin expressed by formula 1 as solid support,

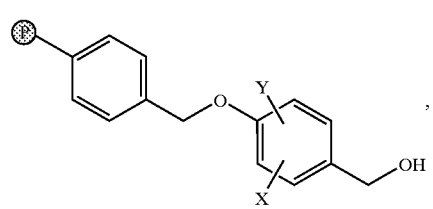

(1)

wherein Ⓟ represents polystyrene-divinylbenzene; X and Y represent hydrogen atom or halogen atom, which may be identical or different, their total number being 1–4; and at least one of them is halogen atom.

6. Quantitative analysis of the product of combinatorial chemical synthesis according to claim 5, wherein the combinatorial chemical synthesis is organic synthesis, peptide synthesis or carbohydrate synthesis.

\* \* \* \* \*